(12) United States Patent
Kassab

(10) Patent No.: US 8,696,584 B2
(45) Date of Patent: Apr. 15, 2014

(54) DEVICES, SYSTEMS AND METHODS FOR DETERMINING FRACTIONAL FLOW RESERVE IN THE PRESENCE OF A CATHETER

(71) Applicant: Ghassan S. Kassab, Zionsville, IN (US)

(72) Inventor: Ghassan S. Kassab, Zionsville, IN (US)

(73) Assignee: 3DT Holdings, LLC, Zionsville, IN (US)

( * ) Notice: Subject to any disclaimer, the term of this patent is extended or adjusted under 35 U.S.C. 154(b) by 0 days.

(21) Appl. No.: 13/646,046

(22) Filed: Oct. 5, 2012

(65) Prior Publication Data

US 2013/0090555 A1 Apr. 11, 2013

Related U.S. Application Data

(60) Provisional application No. 61/543,332, filed on Oct. 5, 2011.

(51) Int. Cl.
*A61B 5/02* (2006.01)
*A61B 5/00* (2006.01)
*A61B 8/14* (2006.01)

(52) U.S. Cl.
USPC ......... 600/486; 600/301; 600/427; 600/468; 600/480; 600/505

(58) Field of Classification Search
USPC ......... 600/301, 381, 427, 468, 479, 480, 485, 600/486, 504, 505, 506; 604/8, 9, 67; 128/898; 606/194
See application file for complete search history.

(56) References Cited

U.S. PATENT DOCUMENTS

| | | | |
|---|---|---|---|
| 2011/0178383 A1* | 7/2011 | Kassab | 600/381 |
| 2011/0178417 A1* | 7/2011 | Kassab | 600/486 |

* cited by examiner

*Primary Examiner* — Michael Rozanski
(74) *Attorney, Agent, or Firm* — Reichel IP LLP; Mark C. Reichel; Kevin R. Erdman

(57) ABSTRACT

Devices, systems, and methods for obtaining fractional flow reserve in the presence of a catheter. In a method of determining a fractional flow reserve in the presence of a catheter, the method comprises the steps of obtaining measurements of an inner luminal organ diameter proximal to, at, and distal to a stenosis and a length of the stenosis, obtaining a pressure drop measurement at the stenosis, calculating a volumetric flow of fluid through the inner luminal organ at the stenosis, and determining a stenotic pressure drop at the stenosis corresponding to dimensions of the guidewire as a function of the calculated volumetric flow of fluid through the inner luminal organ at the stenosis, wherein the stenotic pressure drop is indicative of a fractional flow reserve at or near the stenosis.

18 Claims, 4 Drawing Sheets ately 0.020". In an additional embodiment, the step of obtaining a pressure drop measurement at the stenosis is performed using a pressure catheter having a known outer diameter of 0.020" or approximately 0.020".

DEVICES, SYSTEMS AND METHODS FOR DETERMINING FRACTIONAL FLOW RESERVE IN THE PRESENCE OF A CATHETER

PRIORITY

The present application is related to, and claims the priority benefit of, U.S. Provisional Patent Application Ser. No. 61/543,332, filed Oct. 5, 2011, the contents of which are incorporated by reference in their entirety into this disclosure.

BACKGROUND

Fractional flow reserve (FFR) is a technique for measuring differences in pressure across an arterial stenosis, with the measurement itself being useful to determine the severity of the stenosis. The guidelines for stenotic lesion treatment using FFR have been established based on dimension of a 0.014" outer-diameter pressure wire. It has been shown that this dimension does not significantly affect FFR measurement in the critical range of 0.75-0.8.

By way of example, a patient's luminal organ (such as an artery, for example), may have a 2 mm inner diameter at a location without a lesion, and a 1 mm in diameter at the lesion site. A 0.014" (0.356 mm) diameter wire is approximately half of the diameter of an inner diameter of a vessel at a lesion location if the inner diameter is 1 mm. Advancing a catheter over the pressure wire, such as a 0.02" outer diameter catheter), adds nearly 50% in size to the overall device, which has severe implications with respect to obtaining an accurate FFR measurement.

In view of the foregoing, methods for determining accurate FFR measurements in the view of catheters having dimensions larger than established guideline devices, and devices and systems for facilitating the same, would be appreciated in the marketplace.

BRIEF SUMMARY

In an exemplary embodiment of a method of determining a fractional flow reserve in the presence of a catheter of the present disclosure, the method comprises the steps of obtaining measurements of an inner luminal organ diameter proximal to a stenosis, an inner luminal organ diameter at the stenosis, an inner luminal organ diameter distal to the stenosis, and a length of the stenosis, obtaining a pressure drop measurement at the stenosis using a catheter having a known outer diameter, calculating a volumetric flow of fluid through the inner luminal organ at the stenosis based upon the pressure drop measurement at the stenosis using the catheter, the inner luminal organ diameter proximal to the stenosis, the inner lumen diameter distal to the stenosis, the length of the stenosis, and a difference between the known outer diameter of the catheter and a known outer diameter of a guidewire, and determining a stenotic pressure drop at the stenosis corresponding to dimensions of the guidewire as a function of the calculated volumetric flow of fluid through the inner luminal organ at the stenosis, wherein the stenotic pressure drop is indicative of a fractional flow reserve at or near the stenosis. In another embodiment, the fractional flow reserve is useful to determine a functional assessment of stenosis severity. In an additional embodiment, the method further comprises the step of determining a functional assessment of stenosis severity using the fractional flow reserve. In yet another embodiment, the step of obtaining a pressure drop measurement at the stenosis is performed using a pressure catheter. In an additional embodiment, the step of obtaining a pressure drop measurement at the stenosis is performed using a pressure catheter having a known outer diameter of 0.020" or approximately 0.020".

In an exemplary embodiment of a method of determining a fractional flow reserve in the presence of a catheter of the present disclosure, the step of determining the stenotic pressure drop at the stenosis is further based upon a function of the inner luminal organ diameter proximal to the stenosis, the inner luminal organ diameter at the stenosis, the inner luminal organ diameter distal to the stenosis, and the length of the stenosis. In an additional embodiment, the step of obtaining measurements is performed using the guidewire. In yet an additional embodiment, the step of obtaining measurements is performed using an impedance guidewire having a known outer diameter equivalent to the known outer diameter of the guidewire. In another embodiment, the step of obtaining measurements is performed using an impedance guidewire having two outer excitation electrodes and two inner detection electrodes, wherein the excitation electrodes are operable to generate an electric field within a luminal organ that can be detected by the detection electrodes. In yet another embodiment, the step of obtaining measurements is performed using a procedure selected from the group consisting of (i) angiography and intravascular ultrasound and (ii) angiography and optical coherence tomography.

In an exemplary embodiment of a method of determining a fractional flow reserve in the presence of a catheter of the present disclosure, the step of obtaining a pressure drop measurement is performed using a pressure catheter. In another embodiment, the step of obtaining a pressure drop measurement is performed using the catheter having a pressure sensor. In yet another embodiment, the difference between the known outer diameter of the catheter and the known outer diameter of the guidewire is 0.006" or approximately 0.006".

In an exemplary embodiment of a system for determining a fractional flow reserve of the present disclosure, the system comprises a mechanism configured to obtain measurements of an inner luminal organ diameter proximal to a stenosis within a mammalian body, an inner luminal organ diameter at the stenosis, an inner luminal organ diameter distal to the stenosis, and a length of the stenosis, and a catheter having at least one pressure sensor, the catheter configured to fit around a guidewire and further configured to obtain a pressure drop measurement at the stenosis, and a data acquisition and processing system configured to calculate a volumetric flow of fluid through the inner luminal organ at the stenosis and to determine a stenotic pressure drop at the stenosis as a function of the calculated volumetric flow of fluid through the inner luminal organ at the stenosis, wherein the stenotic pressure drop is indicative of a fractional flow reserve at or near the stenosis. In another embodiment, the mechanism comprises an impedance guidewire. In yet another embodiment, the impedance guidewire comprises two outer excitation electrodes and two inner detection electrodes, wherein the excitation electrodes are operable to generate an electric field within a luminal organ that can be detected by the detection electrodes. In an additional embodiment, the impedance guidewire has an outer diameter of 0.014" or approximately 0.014". In yet an additional embodiment, the mechanism is elected from the group consisting of an angiography device, an intravascular ultrasound device, and an optical coherence tomography device.

In an exemplary embodiment of a system for determining a fractional flow reserve of the present disclosure, the catheter comprises a pressure catheter. In an additional embodiment, the catheter has a known outer diameter of 0.020" or approximately 0.020". In yet an additional embodiment, the data acquisition and processing system is configured to calculate the volumetric flow of fluid through the inner luminal organ at the stenosis based upon the pressure drop measurement, the inner luminal organ diameter proximal to the stenosis, the inner lumen diameter distal to the stenosis, the length of the stenosis, and a difference between a known outer diameter of the catheter and a known outer diameter of a guidewire. In another embodiment, the known outer diameter of the catheter is 0.020" or approximately 0.020", and wherein the known outer diameter of the guidewire is 0.014" or approximately 0.014". In yet another embodiment, the fractional flow reserve is useful to determine a functional assessment of stenosis severity.

In an exemplary embodiment of a method of determining a fractional flow reserve in the presence of a catheter of the present disclosure, the method comprises the steps of obtaining measurements of an inner luminal organ diameter proximal to a stenosis, an inner luminal organ diameter at the stenosis, an inner luminal organ diameter distal to the stenosis, a length of the stenosis, and a pressure drop measurement at the stenosis using a catheter having a known outer diameter, calculating a volumetric flow of fluid through the inner luminal organ at the stenosis based upon the pressure drop measurement at the stenosis using the catheter, the inner luminal organ diameter proximal to the stenosis, the inner lumen diameter distal to the stenosis, the length of the stenosis, and a difference between the known outer diameter of the catheter and a reference device diameter, and determining a stenotic pressure drop at the stenosis corresponding to a reference device diameter as a function of the calculated volumetric flow of fluid through the inner luminal organ at the stenosis, wherein the stenotic pressure drop is indicative of a fractional flow reserve at or near the stenosis. In another embodiment, the fractional flow reserve is useful to determine a functional assessment of stenosis severity. In yet another embodiment, the step of obtaining measurements is performed using the having a known outer diameter of 0.020" or approximately 0.020".

In an exemplary embodiment of a method of determining a fractional flow reserve in the presence of a catheter of the present disclosure, the step of determining the stenotic pressure drop at the stenosis is further based upon a function of the inner luminal organ diameter proximal to the stenosis, the inner luminal organ diameter at the stenosis, the inner luminal organ diameter distal to the stenosis, and the length of the stenosis. In an additional embodiment, the step of obtaining measurements is performed using the catheter having a pressure sensor, two outer excitation electrodes, and two inner detection electrodes, wherein the excitation electrodes are operable to generate an electric field within a luminal organ that can be detected by the detection electrodes, and wherein the pressure sensor can obtain the pressure drop measurement. In yet an additional embodiment, the difference between the known outer diameter of the catheter and the reference device diameter is 0.006" or approximately 0.006".

In an exemplary embodiment of a system for determining a fractional flow reserve of the present disclosure, the system comprises a catheter configured to obtain measurements of an inner luminal organ diameter proximal to a stenosis within a mammalian body, an inner luminal organ diameter at the stenosis, an inner luminal organ diameter distal to the stenosis, a length of the stenosis, and a pressure drop measurement at the stenosis. In another embodiment, the system further comprises a data acquisition and processing system configured to calculate a volumetric flow of fluid through the inner luminal organ at the stenosis and to determine a stenotic pressure drop at the stenosis as a function of the calculated volumetric flow of fluid through the inner luminal organ at the stenosis, wherein the stenotic pressure drop is indicative of a fractional flow reserve at or near the stenosis. In yet another embodiment, the catheter comprises two outer excitation electrodes and two inner detection electrodes, wherein the excitation electrodes are operable to generate an electric field within a luminal organ that can be detected by the detection electrodes. In an additional embodiment, the catheter further comprises a pressure sensor configured to can obtain the pressure drop measurement.

In an exemplary embodiment of a system for determining a fractional flow reserve of the present disclosure, the data acquisition and processing system is configured to calculate the volumetric flow of fluid through the inner luminal organ at the stenosis based upon the pressure drop measurement, the inner luminal organ diameter proximal to the stenosis, the inner lumen diameter distal to the stenosis, the length of the stenosis, and a difference between the known outer diameter of the catheter and a reference device diameter. In an additional embodiment, the reference device diameter is 0.014" or approximately 0.014". In yet an additional embodiment, the catheter has a known outer diameter of 0.020" or approximately 0.020". In another embodiment, the fractional flow reserve is useful to determine a functional assessment of stenosis severity. In yet another embodiment, the catheter is configured to fit around a guidewire and further configured to obtain a pressure drop measurement at the stenosis.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein.

Figure 1:
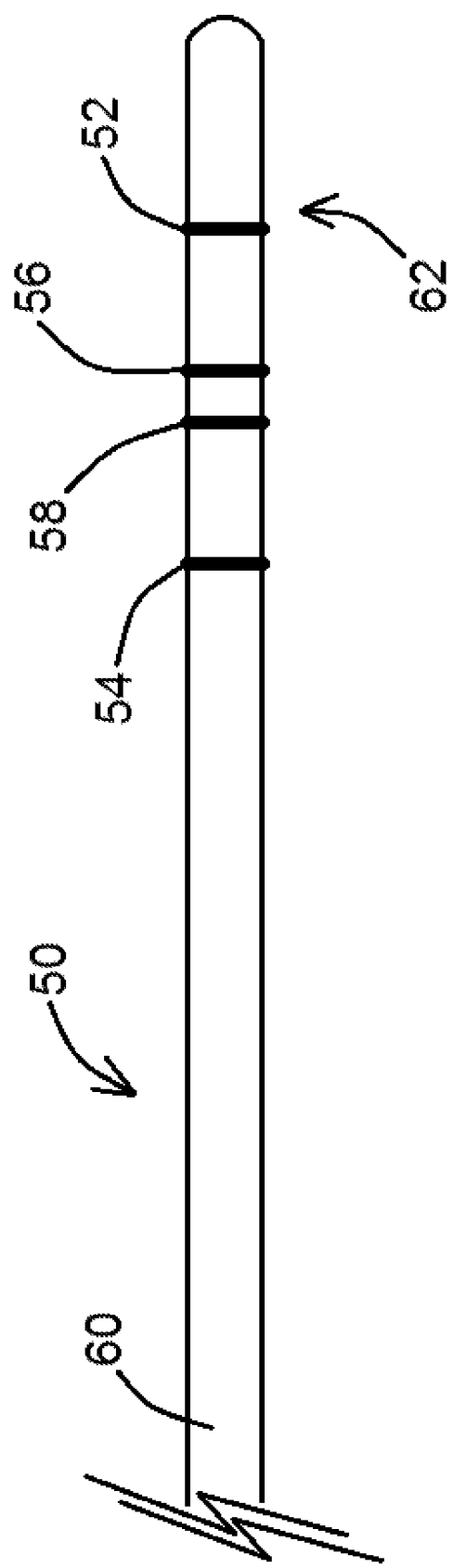
FIG. 1 shows a device useful for obtaining impedance measurements.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Advantages exist to measuring FFR using a catheter over a standard workhorse guidewire or an impedance wire. Naturally the catheter must have an outer diameter greater than the wire (such as a 0.014" guidewire or impedance wire) since it is advanced over the wire.

The guidelines for lesion treatment using FFR have been established based on a dimension of 0.014" (such as a 0.014" pressure wire). It has been shown that this dimension does not significantly affect FFR measurement in the critical range of 0.75-0.8. In theory, a larger diameter than 0.014" will increase the pressure drop and hence decrease FFR (i.e., overestimate the severity of the lesion). Hence, it is important to provide a physics-based correction of FFR due to a measurement device that exceeds 0.014" dimension. The foregoing analysis provides a solution.

An exemplary wire useful to obtain one or more FFR measurements is shown in FIG. 1. Such a wire, for example, may be a wire disclosed within U.S. Patent Application Publication Nos. 20110178383 and 20110178417 of Kassab, having an outer diameter of 0.014" and a series of impedance electrodes positioned thereon. As shown in FIG. 1, an exemplary prior art device 50 may have an impedance portion comprising two outer excitation electrodes 52, 54 and two inner detection electrodes 56, 58 positioned along a body 60 of device 50 at or near the distal end 62 of body 50. The two excitation electrodes 56, 58 are operable to generate an electric field that can be detected by the two inner detection electrodes 56, 58. This combination of electrodes is useful to obtain a series of impedance measurements within a patient's luminal organ in the presence of injected fluid(s) having known conductances and/or a fluid native to the luminal organ, such as the patient's blood, with said impedance measurements useful to obtain luminal cross-sectional areas, fluid velocity through the luminal organ, and the like.

Figure 2:
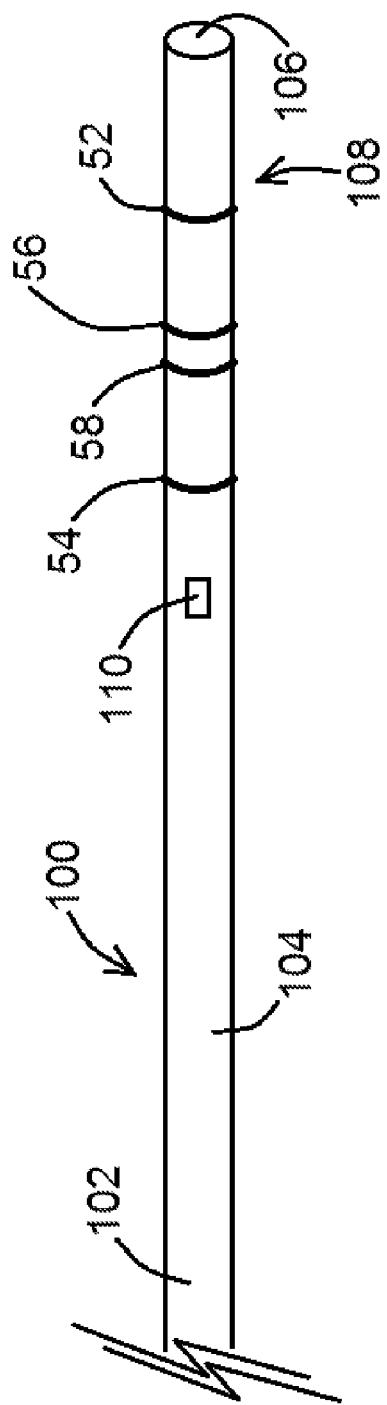
FIG. 2 shows a device useful for obtaining at least one FFR measurement, according to an exemplary embodiment of the present disclosure.

At least another device useful to obtain one or more FFR measurements of the present application is shown in FIG. 2. As shown in FIG. 2, device 100 comprises a catheter 102 having a body 104 and a lumen 106 defined therethrough. Device 100, as shown in FIG. 2, comprises two outer excitation electrodes 52, 54 and two inner detection electrodes 56, 58 positioned along body 104 of device 100 at or near the distal end 108 of body 100. In addition, and as shown in FIG. 2, device 100 has a pressure sensor 110 thereon, whereby one or more pressure measurements, as referenced in further detail herein, can be obtained. Devices 100, in various embodiments, are configured to fit around a guidewire and further configured to allow one or more therapeutics, fluids, and/or the like to be delivered through lumen 106 into a patient's body.

In at least another embodiment, an exemplary device 100 comprises a catheter 102 having a pressure sensor 110 thereon, whereby catheter has no outer excitation electrodes 52, 54 or inner detection electrodes 56, 58. Such an embodiment of device 100, useful to obtain one or more FFR measurements as referenced herein, would be used in connection with a device 50 or another procedure, such as angiography, intravascular ultrasound (IVUS), or optical coherence tomography (OCT), for example.

Figure 3:
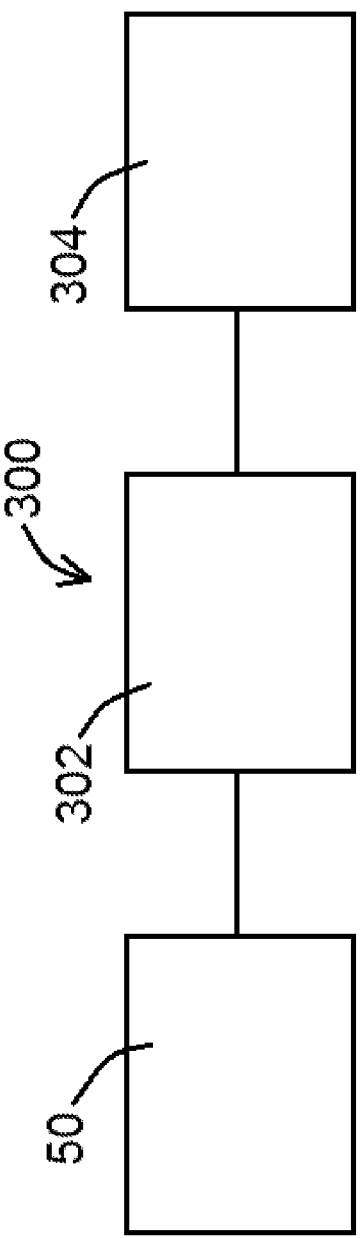
FIG. 3 shows a block diagram of a system useful for obtaining at least one FFR measurement, according to an exemplary embodiment of the present disclosure.

FIG. 3 shows a block diagram of components of an exemplary system of the present disclosure. As shown in FIG. 3, system 300 comprises an exemplary device 50 of the present disclosure, a catheter 302 configured to fit around device 50, and an optional data acquisition and processing system 304 configured to receive and/or process data from device 50 and/or catheter 302.

By way of background, myocardial FFR is known as functional parameter of stenosis severity. FFR during hyperemic flow is expressed as:

$$FFR = \frac{P_{distal} - P_v}{P_a - P_v} \quad [1]$$

wherein $P_a$ is the mean aortic pressure ($P_a \approx P_{proximal}$ assuming no diffuse coronary artery disease), $P_v$ is the central venous pressure, and $P_{proximal}$ and $P_{distal}$ are the hyperemic coronary pressure proximal and distal to stenosis, respectively. If the central venous pressure is assumed to be negligible, Equation [1] is generally approximated as:

$$FFR = \frac{P_{distal}}{P_a} = \frac{P_a - \Delta P}{P_a} \quad [2]$$

where $\Delta P$ is the pressure gradient along the axis of vessel segment from proximal to distal position of stenosis.

Figure 4:
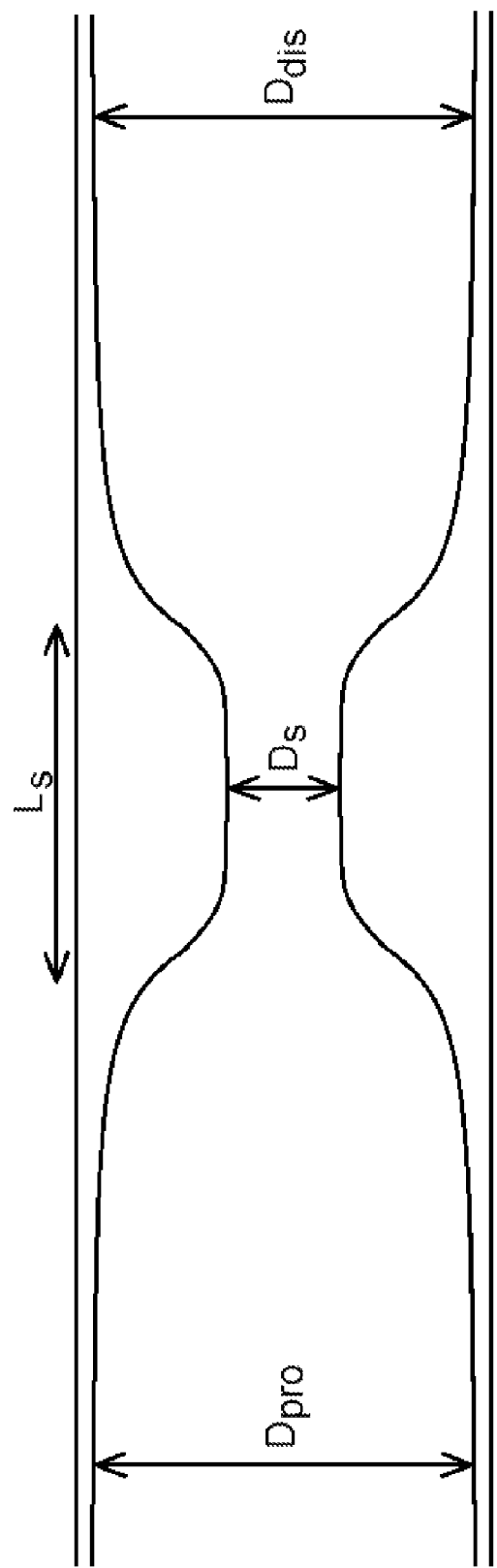
FIG. 4 shows a cross-sectional side view of an exemplary luminal organ having a stenosis therein.

In at least one embodiment of a method of the present disclosure, the method is useful to determine an accurate FFR measurement using any number of catheters having an outer diameter larger than the workhorse impedance wire (i.e., larger than 0.014"). FIG. 4 shows a cross-sectional side view of an exemplary luminal organ having a stenosis therein. Various dimensions are shown in FIG. 4, including an inner diameter proximal to the stenosis (identified as $D_{pro}$), an inner diameter at the stenosis ($D_s$), an inner diameter distal to the stenosis ($D_{dis}$), and the length of the stenosis itself ($L_s$). Such dimensions may be measured using the device shown in FIG. 1, as angiography alone would not be sufficient to provide the required accuracy (either IVUS or OCT would also be required).

In at least one embodiment of a method 100 of the present disclosure, $\Delta P$ is equal to a function of the inner diameter proximal to the stenosis ($D_{pro}$), the inner diameter at the stenosis ($D_s$), the inner diameter distal to the stenosis ($D_{dis}$), the length of the stenosis itself ($L_s$), and the volumetric flow of a fluid (such as blood) through the stenosis (Qs), identified as follows:

$$\Delta P = f(D_{dis}, D_{pro}, D_s, L_s, Q_s) \quad [3]$$

The form of this analytic equation involves various energy dissipation terms in form of integrals as referenced in, for example, U.S. Patent Application Publication Nos. 20110178383 and 20110178417 of Kassab.

As referenced herein, an exemplary standard workhorse impedance wire has an outer diameter of 0.014". The calculations herein are based on such a configuration, which are consistent with current guidelines for lesion treatment using FFR as referenced above. Any catheter that would then be advanced over the wire would be larger than 0.014", and for the purposes of the present exemplary method, the outer diameter of the catheter ($D_{out}$) would be calculated as follows:

$$D_{out} = 0.014" + \delta \quad [4]$$

wherein $\delta$ is the difference $D_{out}$ between and 0.014".

If a catheter of dimension $D_{out}$ is positioned across the stenosis, a pressure gradient change at the stenosis ($\Delta P_{cath}$)

can be measured. After the measurements of $\Delta P_{cath}$, $D_{dis}$, $D_{pro}$, $D_s$, $L_s$ are obtained, $Q_s$ can be calculated as the positive root of the following equation $$\Delta P_{cath} = f(D_{dis} + \delta, D_{pro} + \delta, L_s, Q_s) \quad [5]$$

whereby the relation is quadratic in terms of $Q_s$ and hence will yield two solutions, namely $\pm Q_s$. Once $Q_s$ is determined, the following relation will provide the desired solution for pressure drop corresponding to 0.014" device:

$$\Delta P_{0.014"} = f(D_{dis}, D_{pro}, D_s, L_s, Q_s) \quad [6]$$

Clearly, $\Delta P_{0.014"} < \Delta P_{cath}$, which provides the corrected estimate of pressured drop and hence FFR for functional assessment of lesion severity that conforms with established clinical guidelines. The only assumption here is that flow is less sensitive to stenosis than pressure, i.e., flow changes less in the presence of a catheter than pressure. This assumption is well accepted and forms the rationale for the use of pressure measurement as a surrogate for FFR which is fundamentally a flow index.

As for the form of Equation [3] referenced above, the law of conservation of mass (the general Bernoulli equation) can be written as:

$$\Delta P = \Delta P_{convective} + \Delta P_{constriction} + \Delta P_{diffusive} + \Delta P_{expansion} \quad [7]$$

wherein $\Delta P_{convective}$, $\Delta P_{constriction}$, $\Delta P_{diffusive}$, and $\Delta P_{expansion}$ are energy losses due to flow convection, sudden constriction in CSA from proximal normal vessel to stenosis, flow diffusion, and sudden expansion in CSA from stenosis to distal normal vessel, respectively. In addition, $$\Delta P_{convective} = \frac{\rho Q^2}{2}\left(\frac{1}{CSA_{outlet}^2} - \frac{1}{CSA_{inlet}^2}\right) \quad [8]$$

where $CSA_{inlet}$ and $CSA_{outlet}$ are the inlet and outlet cross-sectional areas, respectively, Q is the hyperemic flow rate in a vessel segment, and $\rho$ is the density of blood. If the flow transition, from proximal normal vessel to stenosis, is well-bound and follows the streamlines, the energy loss due to sudden constriction is relatively small (loss coefficient<<0.1 generally) and negligible such that $\Delta P_{constriction} = 0$.

Although $\Delta P_{diffusive}$ is generally caused by the viscosity in the fully-developed region (i.e., viscous energy loss as referenced herein), the pressure drop serves both to accelerate the flow and to overcome viscous drag in the entrance region of a stenosis, which contributes to the diffusive energy loss. For the entrance region of stenosis, a dimensionless radius of the inviscid core ($\alpha$) can be defined, in which the flow velocity is uniform such as $\alpha = r$ at the inlet, $0 < \alpha < r$ from the inlet to the fully-developed region, and $\alpha = 0$ at the fully-developed region. The dimensionless radius of inviscid core ($\alpha$) can then be calculated from:

$$\frac{\pi \mu L_{stenosis}}{4 \rho Q} = \frac{1}{4}\int_\alpha^1 \frac{(1-\alpha)(6+\alpha)(1+4\alpha+9\alpha^2+4\alpha^3)}{5\alpha(3+2\alpha)(3+2\alpha+\alpha^2)^2} d\alpha \quad [9]$$

where $L_{stenosis}$ is the length of stenosis, and $L_{vessel}$ is the length of vessel, which is comprised of both normal vessel and stenosis. If $\alpha \geq 0.05$ (as shorter lesions <3 cm, which is most typical for coronary arteries), $\Delta P_{diffusive}$ and $\Delta P_{expansion}$ are expressed as:

$$\Delta P_{diffusive}^{\alpha \geq 0.05} = \frac{\rho Q^2}{2 \cdot CSA_{stenosis}^2} \frac{96}{5} \int_\alpha^1 \frac{(1+4\alpha+9\alpha^2+4\alpha^3)}{\alpha(3+2\alpha)(3+2\alpha+\alpha^2)^2} d\alpha + \int_0^{L_{vessel}-L_{stenosis}} \frac{8\pi\mu}{CSA^2} Q dx \text{ and} \quad [10]$$

$$\Delta P_{expansion}^{\alpha \geq 0.05} = \quad [11]$$
$$\frac{\rho Q^2}{2} \cdot \left\{\left(\frac{1}{CSA_{stenosis}} - \frac{1}{CSA_{distal}}\right)^2 + \left[2 \cdot \left(\frac{1}{CSA_{stenosis}} - \frac{1}{CSA_{distal}}\right) \cdot \left(\frac{1}{CSA_{stenosis}} - \frac{1}{3} \cdot \frac{1}{CSA_{distal}}\right) - \left(\frac{1}{CSA_{stenosis}} - \frac{1}{CSA_{distal}}\right)^2\right] \cdot (1-\alpha)^2 \right\}$$

If $\alpha < 0.05$ (longer lesions, >3 cm, less typical), the entire stenosis is divided into entrance and fully-developed regions and the entrance length ($L_{entrance}$) is obtained from $$\frac{\pi \mu L_{entrance}}{4 \rho Q} = \frac{1}{4}\int_{0.05}^1 \frac{(1-\alpha)(6+\alpha)(1+4\alpha+9\alpha^2+4\alpha^3)}{5\alpha(3+2\alpha)(3+2\alpha+\alpha^2)^2} d\alpha \quad [12]$$

such that:

$$\Delta P_{diffusive}^{\alpha < 0.05} = \frac{\rho Q^2}{2 \cdot CSA_{stenosis}^2} \frac{96}{5} \int_{0.05}^1 \frac{(1+4\alpha+9\alpha^2+4\alpha^3)}{\alpha(3+2\alpha)(3+2\alpha+\alpha^2)^2} d\alpha + \int_0^{L_{vessel}-L_{entrance}} \frac{8\pi\mu}{CSA^2} Q dx \text{ and} \quad [13]$$

$$\Delta P_{expansion}^{\alpha < 0.05} = \quad [14]$$
$$\rho Q^2 \cdot \left(\frac{1}{CSA_{stenosis}} - \frac{1}{CSA_{distal}}\right) \cdot \left(\frac{1}{CSA_{stenosis}} - \frac{1}{3} \cdot \frac{1}{CSA_{distal}}\right)$$

In accordance with the foregoing, the entrance effect plus the viscosity (Poiseuille's formula in the fully-developed region) leads to the diffusive energy loss. The energy loss due to sudden expansion in CSA is also taken into account, based on the outlet flow pattern that represents the growth of boundary layer from the inlet of stenosis to the outlet.

As referenced above, one can assume that the flow regime falls in the $\alpha > 0.05$ since most coronary lesions are <2 cm in length and use various equations herein along with the terms for convective and constriction terms (minor in magnitude). Once the flow is determined as outlined above, the $\alpha$ can be recalculated to determine if $\alpha > 0.05$ or $< 0.05$ and to iterate the calculation.

Figure 5:
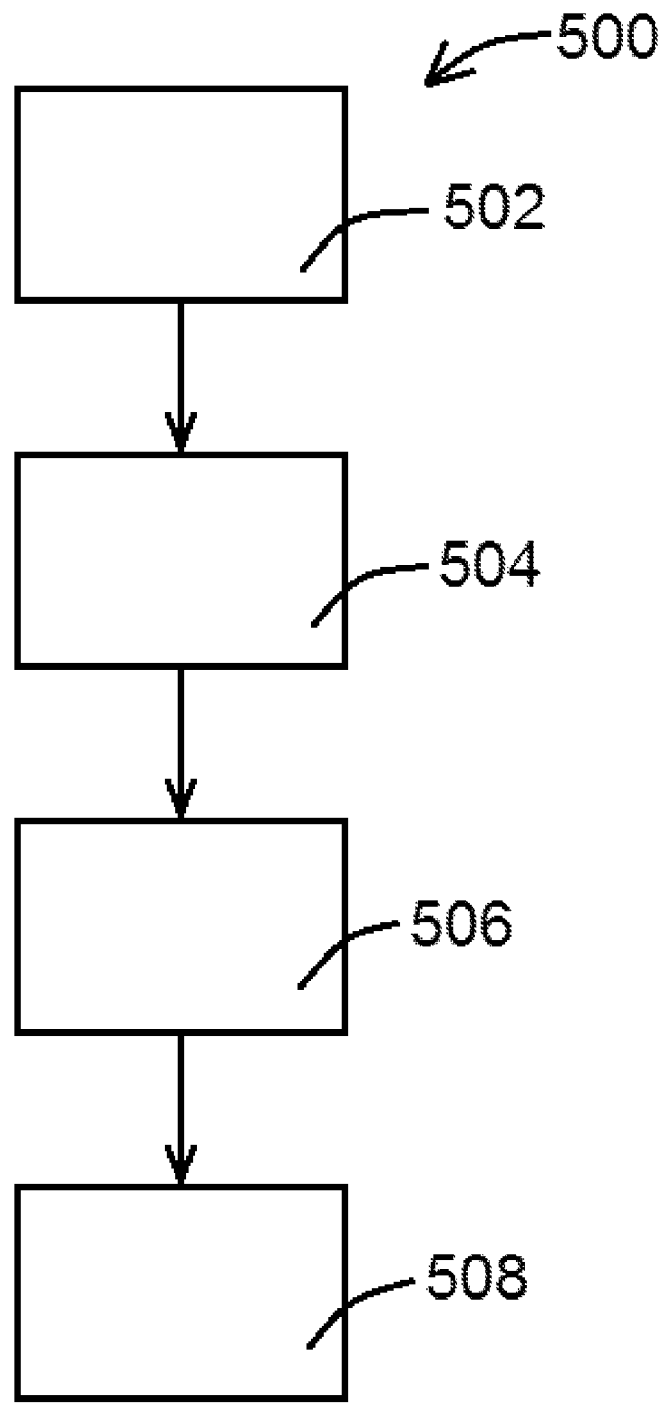
FIG. 5 shows steps of an exemplary method for determining fractional flow reserve in the presence of a catheter, according to an exemplary embodiment of the present disclosure.

In view of the foregoing, steps of an exemplary method of determining FFR of the present disclosure are shown in FIG. 5. As shown in FIG. 5, an exemplary method 500 comprises the steps of obtaining measurements of an inner luminal organ diameter proximal to a stenosis, an inner luminal organ diameter at the stenosis, an inner luminal organ diameter distal to the stenosis, and a length of the stenosis (an exemplary geometry measurement step 502), and the step of obtaining a pressure drop measurement at the stenosis (an exemplary pressure drop measurement step 504). Geometry measurement step 502 may be performed using a device 50 as shown in FIG. 1 or a device 100 as shown in FIG. 2. In other embodiments, geometry measurement step 502 may be performed using angiography, intravascular ultrasound, and optical coherence tomography. Pressure drop measurement step 504 may be performed using a device 100 of the present disclosure, such as a pressure catheter having a known outer diameter of 0.020" or approximately 0.020". Such an exemplary device 100 may comprise, for example, a catheter 102 having a pressure sensor 110, two outer excitation electrodes 52, 54, and two inner detection electrodes 56, 58, wherein the excitation electrodes 52, 54 are operable to generate an electric field within a luminal organ that can be detected by the detection electrodes 56, 58, and wherein the pressure sensor 100 can obtain the pressure drop measurement.

An exemplary method 500 of the present disclosure may further comprise the step of calculating a volumetric flow of fluid through the inner luminal organ at the stenosis based upon the pressure drop measurement at the stenosis using the catheter, the inner luminal organ diameter proximal to the stenosis, the inner lumen diameter distal to the stenosis, the length of the stenosis, and a difference between the known outer diameter of the catheter and a reference device diameter (such as a known outer diameter of a guidewire) (an exemplary volumetric flow calculating step 506). Method 500, in various embodiments, further comprises the step of determining a stenotic pressure drop at the stenosis corresponding to the reference device diameter (such as the dimensions of the guidewire, for example), as a function of the calculated volumetric flow of fluid through the inner luminal organ at the stenosis, wherein the stenotic pressure drop is indicative of a fractional flow reserve at or near the stenosis (an exemplary FFR determination step 508). FFR determination step 508 may be performed, in various embodiments, to determine a functional assessment of stenosis severity. In at least one embodiment, the step of determining a stenotic pressure drop within FFR determination step 508 is further based upon a function of the inner luminal organ diameter proximal to the stenosis, the inner luminal organ diameter at the stenosis, the inner luminal organ diameter distal to the stenosis, and the length of the stenosis. An exemplary difference between the reference device diameter (the outer dimensions of the guidewire, for example) and the outer diameter of the catheter may be 0.006" or approximately 0.006", for example. In such an embodiment, the reference diameter may be 0.014", and the catheter outer diameter may be 0.020".

While various embodiments of devices and systems for obtaining fractional flow reserve in the presence of a catheter and methods of using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A method of determining a fractional flow reserve in the presence of a catheter, the method comprising the steps of:
    obtaining measurements of an inner luminal organ diameter proximal to a stenosis, an inner luminal organ diameter at the stenosis, an inner luminal organ diameter distal to the stenosis, and a length of the stenosis;
    obtaining a pressure drop measurement at the stenosis using a catheter having a known outer diameter;
    calculating a volumetric flow of fluid through the inner luminal organ at the stenosis based upon the pressure drop measurement at the stenosis using the catheter, the inner luminal organ diameter proximal to the stenosis, the inner lumen diameter distal to the stenosis, the length of the stenosis, and a difference between the known outer diameter of the catheter and a known outer diameter of a guidewire; and
    determining a stenotic pressure drop at the stenosis corresponding to dimensions of the guidewire as a function of the calculated volumetric flow of fluid through the inner luminal organ at the stenosis, wherein the stenotic pressure drop is indicative of a fractional flow reserve at or near the stenosis.

2. The method of claim 1, further comprising the step of:
    determining a functional assessment of stenosis severity using the fractional flow reserve.

3. The method of claim 1, wherein the step of obtaining a pressure drop measurement at the stenosis is performed using a pressure catheter.

4. The method of claim 1, wherein the step of determining the stenotic pressure drop at the stenosis is further based upon a function of the inner luminal organ diameter proximal to the stenosis, the inner luminal organ diameter at the stenosis, the inner luminal organ diameter distal to the stenosis, and the length of the stenosis.

5. The method of item 1, wherein the step of obtaining measurements is performed using the guidewire.

6. The method of claim 1, wherein the step of obtaining measurements is performed using an impedance guidewire having a known outer diameter equivalent to the known outer diameter of the guidewire.

7. The method of claim 1, wherein the step of obtaining measurements is performed using a procedure selected from the group consisting of (i) angiography and intravascular ultrasound and (ii) angiography and optical coherence tomography.

8. The method of claim 1, wherein the step of obtaining a pressure drop measurement is performed using an apparatus selected from the group consisting of a pressure catheter and the catheter having a pressure sensor.

9. A system for determining a fractional flow reserve, comprising:
    a mechanism configured to obtain measurements of an inner luminal organ diameter proximal to a stenosis within a mammalian body, an inner luminal organ diameter at the stenosis, an inner luminal organ diameter distal to the stenosis, and a length of the stenosis; and
    a catheter having at least one pressure sensor, the catheter configured to fit around a guidewire and further configured to obtain a pressure drop measurement at the stenosis; and
    a data acquisition and processing system configured to calculate a volumetric flow of fluid through the inner luminal organ at the stenosis and to determine a stenotic pressure drop at the stenosis as a function of the calculated volumetric flow of fluid through the inner luminal organ at the stenosis, wherein the stenotic pressure drop is indicative of a fractional flow reserve at or near the stenosis,
    wherein the data acquisition and processing system is configured to calculate the volumetric flow of fluid through the inner luminal organ at the stenosis based upon the pressure drop measurement, the inner luminal organ diameter proximal to the stenosis, the inner lumen diameter distal to the stenosis, the length of the stenosis, and a difference between a known outer diameter of the catheter and a known outer diameter of a guidewire.

10. The system of claim 9, wherein the mechanism comprises an impedance guidewire.

11. The system of claim 10, wherein the impedance guidewire comprises two outer excitation electrodes and two inner detection electrodes, wherein the excitation electrodes are operable to generate an electric field within a luminal organ that can be detected by the detection electrodes.

12. The system of claim 10, wherein the impedance guidewire has an outer diameter of 0.014" or approximately 0.014".

13. The system of claim 10, wherein a difference between an outer diameter of the catheter and an outer diameter of the guidewire is 0.006" or approximately 0.006".

14. The system of claim 10, wherein the mechanism is elected from the group consisting of (i) an angiography device and an intravascular ultrasound device and (ii) an angiography device and an optical coherence tomography device.

15. The system of claim 9, wherein the known outer diameter of the catheter is 0.020" or approximately 0.020", and wherein the known outer diameter of the guidewire is 0.014" or approximately 0.014".

16. A method of determining a fractional flow reserve in the presence of a catheter, the method comprising the steps of:

obtaining measurements of an inner luminal organ diameter proximal to a stenosis, an inner luminal organ diameter at the stenosis, an inner luminal organ diameter distal to the stenosis, a length of the stenosis, and a pressure drop measurement at the stenosis using a catheter having a known outer diameter;

calculating a volumetric flow of fluid through the inner luminal organ at the stenosis based upon the pressure drop measurement at the stenosis using the catheter, the inner luminal organ diameter proximal to the stenosis, the inner lumen diameter distal to the stenosis, the length of the stenosis, and a difference between the known outer diameter of the catheter and a reference device diameter; and determining a stenotic pressure drop at the stenosis corresponding to a reference device diameter as a function of the calculated volumetric flow of fluid through the inner luminal organ at the stenosis, wherein the stenotic pressure drop is indicative of a fractional flow reserve at or near the stenosis.

17. The method of claim 16, further comprising the step of:
determining a functional assessment of stenosis severity using the fractional flow reserve.

18. The method of claim 16, wherein the step of determining the stenotic pressure drop at the stenosis is further based upon a function of the inner luminal organ diameter proximal to the stenosis, the inner luminal organ diameter at the stenosis, the inner luminal organ diameter distal to the stenosis, and the length of the stenosis.

* * * * *